United States Patent
Osgood et al.

(10) Patent No.: US 7,521,245 B1
(45) Date of Patent: Apr. 21, 2009

(54) METHOD FOR WASHING AND DRYING PINS IN MICROARRAY SPOTTING INSTRUMENTS

(75) Inventors: Avery Osgood, Bellingham, MA (US); Mack J. Schermer, Belmont, MA (US); Marc Silvagni, Beverly, MA (US)

(73) Assignee: PerkinElmer LAS, Inc., Boston, MA (US)

( * ) Notice: Subject to any disclaimer, the term of this patent is extended or adjusted under 35 U.S.C. 154(b) by 1031 days.

(21) Appl. No.: 09/586,858

(22) Filed: Jun. 5, 2000

(51) Int. Cl.
 *G01N 33/00* (2006.01)
(52) U.S. Cl. .................. 436/49; 422/104; 422/63; 422/68.1; 422/100
(58) Field of Classification Search ................ 422/104, 422/63, 68.1, 100, 117, 129; 15/302, 300.1, 15/303, 320, 322; 134/44, 50, 85, 88, 94.1; 435/287.1, 287.3; 264/600, 601; 436/49
See application file for complete search history.

(56) References Cited

U.S. PATENT DOCUMENTS

| | | | |
|---|---|---|---|
| 4,817,443 A | 4/1989 | Champseix et al. | |
| 5,055,263 A | 10/1991 | Meltzer | |
| 5,133,373 A | 7/1992 | Hoffman et al. | |
| 5,306,510 A | 4/1994 | Meltzer | |
| 5,408,891 A | 4/1995 | Barber et al. | |
| 5,411,065 A | 5/1995 | Meador et al. | 141/1 |
| 5,474,744 A | 12/1995 | Lerch | |
| 5,525,515 A | 6/1996 | Blattner | |
| 5,603,342 A | 2/1997 | Shambaugh | |
| 5,700,637 A | 12/1997 | Southern | |
| 5,770,151 A | 6/1998 | Roach et al. | |
| 5,807,522 A | 9/1998 | Brown et al. | |
| 5,827,744 A | 10/1998 | Fose et al. | |
| 5,847,105 A | 12/1998 | Baldeschwieler et al. | |
| 5,895,915 A | 4/1999 | DeWeerd et al. | |
| 5,897,837 A | 4/1999 | Mizuno | |
| 5,922,617 A | 7/1999 | Wang et al. | |
| 5,927,547 A | 7/1999 | Papen et al. | |
| 5,935,859 A | 8/1999 | Elliott et al. | |
| 5,957,167 A | 9/1999 | Feygin | |
| 6,015,880 A | 1/2000 | Baldeschwieler et al. | |
| 6,017,496 A | 1/2000 | Nova et al. | |

(Continued)

FOREIGN PATENT DOCUMENTS

EP  0 287 783  10/1988

(Continued)

OTHER PUBLICATIONS

Anonymous, "Wire Printer Diagnostic Method," IBM Technical Disclosure Bulletin, vol. 27, No. 9, 1985, p. 5042.

(Continued)

*Primary Examiner*—Sam P. Siefke
(74) *Attorney, Agent, or Firm*—Wilmer Cutler Pickering Hale & Dorr LLP (57) ABSTRACT

A method and apparatus are provided for washing and drying pins in a microarray spotting instrument. The apparatus includes an array of chambers, each for receiving one of the pins of the spotting instrument. To wash the pins, streams of wash fluid are directed at the pins. To dry the pins, a gas such as air is flowed over pin surfaces.

16 Claims, 6 Drawing Sheets

U.S. PATENT DOCUMENTS

| | | | |
|---|---|---|---|
| 6,024,925 A | 2/2000 | Little et al. | 422/100 |
| 6,039,211 A | 3/2000 | Slater et al. | 222/1 |
| 6,083,763 A | 7/2000 | Balch | 436/518 |
| 6,101,946 A | 8/2000 | Martinsky | |
| 6,269,846 B1 * | 8/2001 | Overbeck et al. | 141/1 |
| 6,428,752 B1 | 8/2002 | Montagu | 422/104 |

FOREIGN PATENT DOCUMENTS

| | | |
|---|---|---|
| GB | 2 310 006 A | 8/1997 |
| WO | WO 99/22867 | 5/1999 |
| WO | WO 99/34931 | 7/1999 |
| WO | WO 99/36760 | 7/1999 |
| WO | WO 99/42804 | 8/1999 |
| WO | WO 00/01798 | 1/2000 |
| WO | WO 00/13796 | 3/2000 |
| WO | WO 00/51058 | 8/2000 |
| WO | WO 00/63705 | 10/2000 |
| WO | WO 01/58593 | 8/2001 |

OTHER PUBLICATIONS

"Patent Abstracts of Japan," vol. 007, No. 196, Aug. 26, 1983.

Derisi et al, "The Mguide, a Complete Guide to Building Your Own Microarrayer," Biochemistry Department of Stanford University, 1999, pp. 19-20.

Rose, "Application of a Novel Microarraying System in Genomics Research and Drug Discovery," Journal of the Association for Laboratory Automation, vol. 3, No. 3, Jul. 1998, pp. 53-56.

Schummer et al., "Inexpensive Handheld Device for the Construction of High-Density Nucleic Acid Arrays," BioTechniques, vol. 23, No. 6, 1997, pp. 1087-1090.

Website (www.cartesiantech.com) literature of Cartesian Technologies showing specifications of PinArray, nQUAD, CloneTracker and PegaSys printed Jan. 14, 2000.

Website (www.genemachines.com) literature of GeneMachines showing Specifications of OmniGrid printed Jan. 14, 2000.

Website (www.geneticmicro.com) literature of Genetic MicroSystems, Inc. showing specifications of GMS Microarray Analysis System printed on Jan. 14, 2000.

Website (www.genetix.co.uk) literature of Genetix Limited showing specifications of Q Array MicroArrayer printed Jan. 14, 2000.

Website (www.genpakdna.com) literature of GenPak, Inc. showing specifications of genpak Array 21 Robotic Micro-Arrayer System printed on Jan. 14, 2000.

Website (www.genomicsolutions.com) literature of Genomic Solutions, Inc. showing specifications of Flexys printed on Jan. 14, 2000.

Website (www.esit.com) literature of Engineering Services Inc. showing specifications of SDDC printed on Jan. 14, 2000.

Website (www.packardinst.com) literature of Packard Instrument Company showing specifications of The BioChip Arrayer printed on Jan. 17, 2000.

Website (www.arrayit.com) literature of TeleChem International, Inc. showing specifications of ArrayIt printed on Jan. 14, 2000.

Website (www.majerprecision.com) literature of Majer Precision Engineering showing specifications of MicroQuill printed on Jan. 14, 2000.

Website (www.corning.com) literature of Corning Incorporated showing specifications of Corning Microarray Technology (CMT) printed on Jan. 27, 2000.

Website (http://nunc.nalgenunc.com) literature of Nalge Nunc International showing specifications of MicroWell Plates printed Jan. 27, 2000.

Website (www.keyence.com) literature of Keyence Corporation of America showing specifications of CCD Bar Code Readers.

Genetic MicroSystems Product Literature of GMS Microarray Analysis System.

Website (www.sharpmeg.com) literature of Sharp Microelectronics of the Americas showing specifications of Optoelectronic Devices printed on Jan. 28, 2000.

Sharp Product Literature of GP2A20/GP2A22 printed at least as early as Jan. 28, 2000.

Sharp Product Literature of GP2A111 printed at least as early as Jan. 28, 2000.

Mark Schena (editor), "Microarray Biochip Technology", Chapter 2, pp. 19-38 (relevant pp. 33-36 entitled *Pin Washing and Sample Carryover*), Eaton Publishing, BioTechniquest Books Division, Natick, Massachusetts U.S.A.

Website (www.intelligentbio.com) literature of Intelligent Bio-Instruments showing specifications of HT Production Microarrayer printed on Apr. 14, 2000.

Website (www.labman.co.uk) literature of Labman Automation Limited showing specifications of Microarray Spotter systems printed on Apr. 14, 2000.

Alexander Kuklin, Ph.D., "Automation in Microarray Image Processing And Data Mining, High Throughput Screening" (Supplement to Biomedical Products), Jan. 2000, pp. 4, 5, 6, 8, Cahners Publishing, Morris Plains, New Jersey, U.S.A.

Mark Schena, "DNA Microarrays: A Practical Approach", Chapters 2 and 6 (pp. 17-42 and pp. 101-120), New York, Oxford University Press, 1999, ISBN 0-19-963776-8.

GSI Lumonics ScanArray Technical Note 300: ScanArray Microarray Barcodes: Automated Microarray Analysis & Data Tracking, Jun. 1999.

Website (www.biorobotics.co.uk) literature of BioRobotics, Inc. showing specifications of MicroGrid printed Jan. 14, 2000.

* cited by examiner

2 - 3 mm approximate inside diameter

METHOD FOR WASHING AND DRYING PINS IN MICROARRAY SPOTTING INSTRUMENTS

BACKGROUND OF THE INVENTION

1. Field of the Invention

The present invention relates generally to microarray spotting instruments and, more particularly, to a method and apparatus for washing and drying pins in such instruments.

2. Description of Related Art

As is well known (and described, e.g., in U.S. Pat. No. 5,807,522 issued to Brown et al. and in "DNA Microarrays: A Practical Approach," Schena, Mark, N.Y., Oxford University Press, 1999, ISBN 0-19-963776-8), microarrays are arrays of very small samples of purified DNA or protein target material arranged as a grid of hundreds or thousands of small spots on a solid substrate. When the microarray is exposed to selected probe material, the probe material selectively binds to the target spots only where complementary bonding sites occur, through a process called hybridization. Subsequent quantitative scanning in a fluorescent microarray scanner may be used to produce a pixel map of fluorescent intensities (See, e.g., U.S. Pat. No. 5,895,915 issued to DeWeerd et al.). This fluorescent intensity map can then be analyzed by special purpose quantitation algorithms, which reveal the relative concentrations of the fluorescent probes and hence the level of gene expression, protein concentration, etc., present in the cells from which the probe samples were extracted.

Microarray spotting instruments (also known as "spotters") are used to place the small samples of DNA, protein, or other target biological material onto the microarray substrates. The spotting instruments retrieve the target material from wells in a reservoir plates and "print" target spots in arrays on the microarray substrates. The reservoir plates are typically 96-well or 384-well plates, although other types are also used. Microarrays often have thousands or tens of thousands of target spots, with each spot being of a target compound from a different well of a plate.

Figure 1:
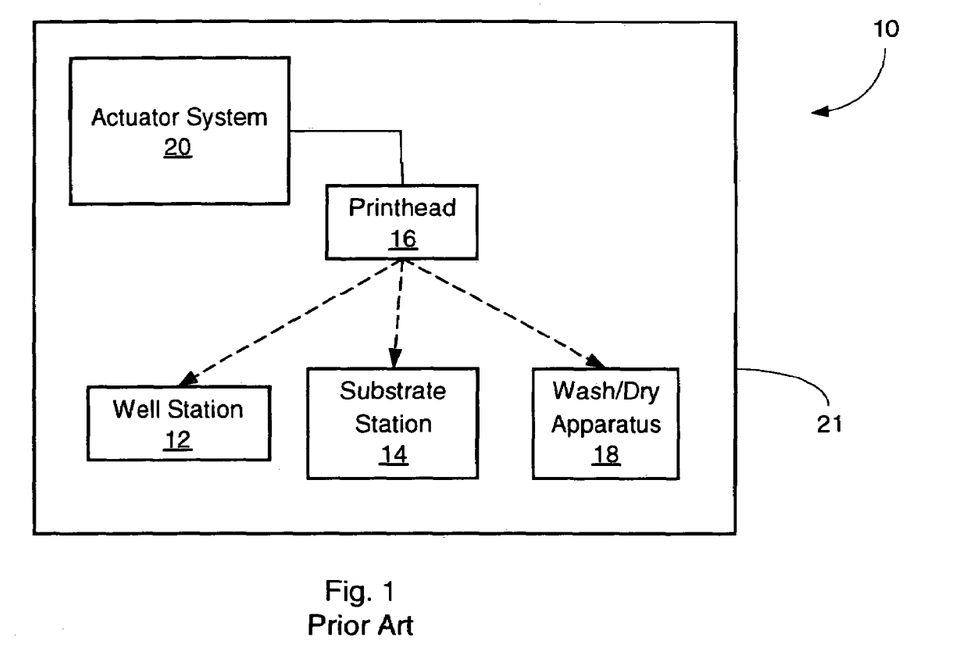
FIG. 1 is a simplified block diagram of a prior art microarray spotting instrument.

FIG. 1 is a simplified block diagram of components of a typical spotter 10. The spotter 10 includes (1) a plate-holding well station 12, which holds one or more reservoir plates, (2) a substrate holding station 14, which holds a plurality of microarray substrates (typically 20-100 substrates), (3) a printhead 16, which holds a plurality of microarray spotting pins (shown, e.g., in FIG. 2), (4) a pin washing and drying apparatus 18, and (5) an actuator system 20, which includes robotic manipulator arms for moving the printhead in X, Y and Z directions relative to the plates, substrates and the washing and drying apparatus. The spotter is enclosed in an enclosure 21 to provide a humidity controlled environment.

Figure 2:
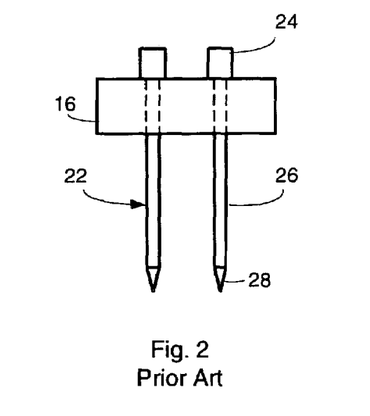
FIG. 2 is a side view of a prior art printhead of the spotting instrument holding microarray pins.

FIG. 2 shows a side view of a simplified printhead 16 holding a plurality of pins 22. For convenience of illustration, only two pins 22 are shown, although a typical printhead will hold many more pins. Pins typically include a pinhead 24, a pin shaft 26 and a tapered pin tip 28. The printhead 16 comprises a block of material, typically metal, that includes an array of through-holes. The through-holes are slightly larger than the outer diameter of the pin shafts 26 so the shafts can extend through the through-holes. The through-holes are also smaller than the outer diameter of the pin heads 24 so that when the pin shaft 26 is dropped into one of the through-holes, the pin head 24 will be supported by the upper surface of the printhead 16. The pins are thereby "slip-fit" into the through-holes of the printhead.

Pins are commercially available in several distinct forms. The simplest pins are solid pins. These pins are simple and robust, but in being dipped into the target material in a well typically only take up enough material to form one spot. This then requires the spotting instrument to dip the pin once for every microarray spot that is to be printed.

Figure 3:
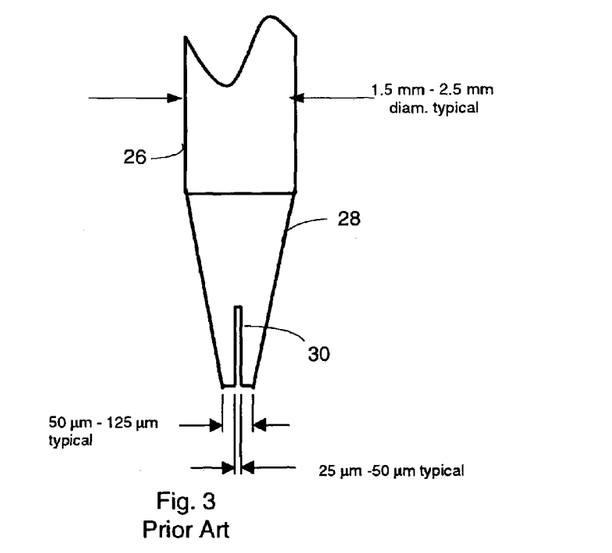
FIG. 3 is an enlarged side view of the tip of a prior art pin having a slot reservoir.

More commonly used pins are multi-spot dispensing pins that can hold enough target material from a sample reservoir to form multiple spots before they need to be re-dipped in the reservoir. One such type of multi-spot dispensing pin is a slotted pin (shown in FIG. 3), which has a gap or slot 30 at the pin tip 28. One example of such a pin is the MicroQuill brand pin available from Majer Precision Engineering, Inc. This type of pin draws fluid into the gap or slot 30 by capillary action, and deposits a small amount onto the substrate. The amount forming a spot is small compared to the sample uptake volume, so that each dip of the pin into sample liquid takes up enough sample material to print about 50-250 nearly identical spots without re-dipping in the sample plate.

A spotting cycle of a microarray spotting instrument 10 for printing a batch of microarrays is generally as follows: (1) the printhead 16 is moved to the well station 12 and positioned such that the pins 22 are located directly above particular respective wells of a reservoir plate; (2) the printhead 16 is lowered to dip the pins in respective wells, allowing each pin to take up an aliquot of sample; (3) the printhead 16 is moved to the substrate station 14 and positioned above the first substrate to be printed; (4) the printhead 16 is lowered, allowing the tips of the pins to make contact with the substrate, thereby depositing spots of target material on the substrate; (5) the printhead 16 is lifted (so that the pins are no longer in contact with the substrate) and moved to a position above the next substrate to be printed, and the printing motion is repeated; (6) printing is repeated until all substrates in the batch have been printed with these particular samples; (7) the printhead 16 is then moved to a pin washer of the wash/dry apparatus 18, and the pins are washed by dipping them in a wash solution; (8) the printhead 16 is moved to the pin dryer also of the wash/dry apparatus 18, where the pins are dried by inserting them in a vacuum dryer; (9) the wash/dry sequence is repeated two or three times; and (10) the printhead 16 is moved to a position such that the pins 22 are above the next target material to be taken up and the entire cycle is repeated until all desired samples have been printed on the batch of substrates.

As indicated above, microarrays are typically spotted in batches, where the spotter is loaded with a plurality of substrates and the spotting operation produces multiple spotted microarrays, all of which are substantially identically printed. Each microarray typically is spotted so that it has between hundreds and tens of thousands of spots, where each spot comprises the dried residue of a liquid droplet transferred or printed by a pin. The printhead is typically fitted with between 4 and 64 pins, which perform all of their operations in parallel.

After printing the last substrate with a given sample, the pins are washed and dried. This step is important because if the remaining sample is not adequately removed from each pin, the subsequent spots printed by the pin will be contaminated by the "carry-over" from the previous sample. Also, samples in wells subsequently dipped will be contaminated when the pin is dipped for sample uptake. Cross-contamination of samples in a microarray or plate would be very problematic in a microarray application because the hybridization and analysis processes occurring after spotting are based on the assumption that each spot is a single, pure sample and not some mixture of unknown proportions.

Figure 4:
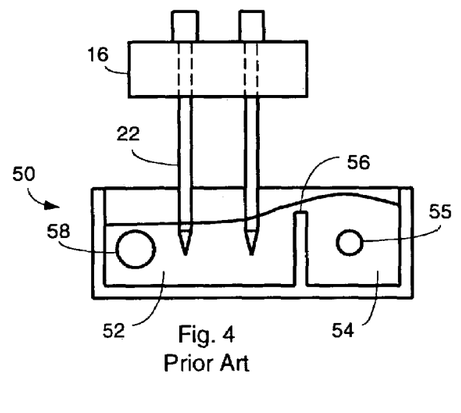
FIG. 4 is a cross-section view of a prior art flowing fluid bath pin washer.

Prior art spotters utilize separate pin washing and pin drying devices at the wash/dry station 18. The washing is typically accomplished by dipping the pin tips into a reservoir of wash fluid, typically distilled or filtered water. FIG. 4 illustrates one prior art pin washer 50, in which the wash fluid is kept flowing through a wash chamber 52, in which the pins are dipped. Wash fluid is introduced into a small, open input chamber 54 by a tube fed by a peristaltic pump. The tube is connected to a wash fluid input port 55. The fluid flows over a weir or dam 56 into the slightly larger washing chamber 52. The two-chamber approach allows any sediment in the wash fluid to settle out in the input chamber 54 before the fluid is brought into contact with the pins 22. A wash fluid output or drain port 58 drains fluid from the chamber 52.

Dipping the pin tips in the fluid in the wash chamber 52 causes the pins 22 to take up wash fluid by capillary action in the pin tip slot 30, similar to the way the pins take up sample from the reservoir plates. This dilutes the remaining sample in the pin slot reservoirs.

Figure 5:
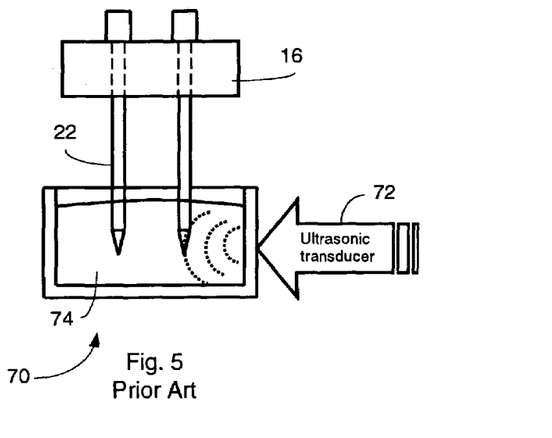
FIG. 5 is a cross-section view of a prior art ultrasonic pin washer.

As shown in FIG. 5, in another prior art wash device 70, an ultrasonic transducer 72 (sometimes called a sonicator) is provided to introduce micro-cavitation in the wash fluid in the wash chamber 74. Sonication is a more effective washing process than the dipping and diluting process of FIG. 4. However, repeated sonication is not recommended because the split tips of pins (defining the slot 30) can act as tuning forks and resonate sympathetically with the ultrasonic signal. This can lead to the pin tip oscillating at high amplitudes and damaging the critical and fragile surfaces near the pin tip.

With the prior art dipping type pin washers, there is a possibility of cross-contamination between pins. The pins of a printhead, which have multiple sample types on them, are dipped simultaneously in the wash fluid, which is a liquid solvent chosen for its ability to dissolve the reagents carried by the pins. The pins are typically only 4.5 to 9.0 mm apart, and some transport of mass from one pin to another during the dip washing process is inevitable even though the likelihood of gross contamination is small.

Figure 6:
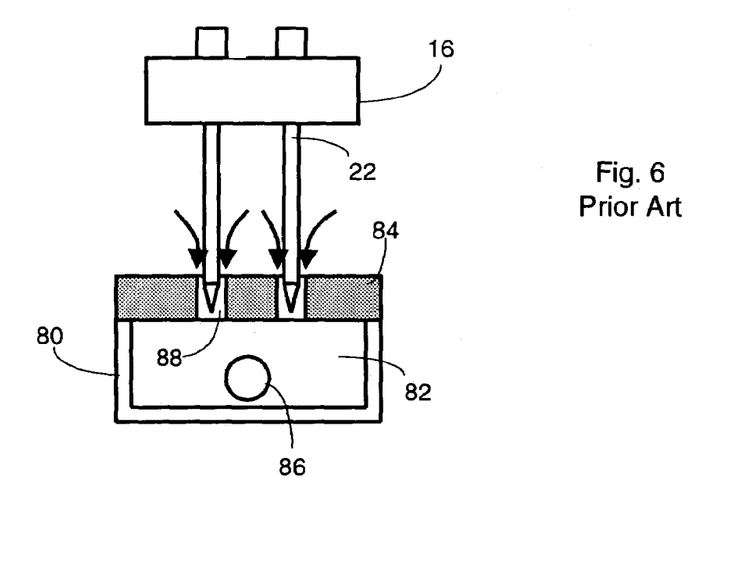
FIG. 6 is a cross-section view of a prior art pin dryer.

The pins are then withdrawn from the wash fluid and the printhead is moved to a separate pin drying device. A typical prior art pin dryer 80 is shown in FIG. 6. The pin dryer 80 works by applying vacuum to a plenum chamber 82 below a dryer top plate 84. A vacuum line connects a vacuum pump to the chamber 82 through a port 86. The pin tips are inserted into holes 88 in the dryer top plate 84, and the vacuum below causes ambient air to flow past the pin tips at high velocity and low pressure. These conditions cause the pins, including the slot fluid reservoir in the pin tip, to be dried in about 2-10 seconds. Since the fluid that was dried in and on the pin was diluted by the first washing step, and not entirely washed away, dried residue of diluted sample remains on the pin surface after drying. For this reason, the washing step is repeated at least twice and sometimes as many as four times, with each washing causing a further dilution of the residue in and on the pin until it is inconsequential.

The performance of a vacuum pin dryer 80 depends on the velocity of the air drawn past the pins and on the humidity of that air. Many spotters provide humidity-controlled environments within their enclosures 21, with humidity typically about 55%-65%. Air with that level of humidity is considerably less effective for drying pins than air at the 30%-45% humidity levels most commonly found in office and laboratory environments. The drying time and/or the air velocity must be increased to retain dryer effectiveness at the higher humidity level. Also, vacuum dryers that obtain their air supply from the humidified enclosure 21 generally pump that humidified air out to the atmosphere, placing an additional load on external humidity generating mechanisms and humidity controlling mechanisms.

Prior art dryers typically utilize vacuum pumps of linear piston or rotary vane type, with volume flow ratings in the 1-5 cfm range. When these pumps are applied to dryers with 32 or more pin holes, the air velocity around the pins is generally in the 2-10 m/sec range. Under these conditions, drying times are rarely less than 3 seconds and can be as long as 10 seconds or more. In some instruments, users often block off any dryer holes not being used (as the printhead is often not fully populated with pins) with tape, to increase the velocity of the air in the holes of the dryer that are being used.

The timing of a typical prior art spotting cycle for printing material from one dip into the sample plate onto a batch of 20 microarrays is as shown in the following table:

| Operation | Time (sec.) | Number of operations per cycle | Total time (sec.) |
|---|---|---|---|
| Move to sample plate position, dip pins, and withdraw pins. | 3 | 1 | 3 |
| Move to first printing position over a substrate, print, and withdraw pins. | 1.2 | 1 | 1.2 |
| Move to next substrate, print, and withdraw pins (repeated 19 more times). | 1.2 | 19 | 22.8 |
| Move to washer, dip, and withdraw | 2 | 3 | 6 |
| Move to dryer, insert pins, hold in dryer for three seconds, and withdraw pins. | 4 | 3 | 12 |
| Total time | | | 45 |

Of the 45 seconds needed for one printing cycle, 18 seconds or 40% of the time is spent on washing and drying the pins. Accordingly, a quicker washing/drying process would significantly increase the throughput of the spotting instrument.

Many Microarrays have over 10,000 unique spots printed on them. Most printheads are fitted with no more than 8 or 16 pins since, greater numbers of pins cause the footprint of the printed array to be large, which leads to experimental complications at a downstream hybridization step. Printing 10,000 spots with 16 pins requires 625 dip—print—wash/dry cycles in the spotter. Printing 10,000 spots with 8 pins requires 1,250 cycles, of which over six hours (22,500 seconds) is devoted to washing and drying. Thus, the amount of time required to perform the washing and drying can be a significant portion of the total time required to spot a batch of microarrays and also can be a long time period per batch in absolute terms.

A need exists for a faster and more efficient method and apparatus for washing and drying microarray spotting pins in order to improve the throughput of microarray spotting instruments.

BRIEF SUMMARY OF THE INVENTION

The present invention is directed to a method and apparatus for quickly and efficiently washing and drying spotting pins used in the operation of microarray spotting instruments. The apparatus includes a housing having an array of upstanding tubes, each defining a chamber for receiving one of the pins of the spotting instrument. To wash the pins, streams of wash fluid are directed at the pins through inlet ports in the tubes. To dry the pins, a gas such as air is flowed through the tubes over pin surfaces. Pins can thereby be washed and dried without having to be moved. The gas used in drying the pins is preferably air of low humidity from outside an enclosure containing the spotting instrument in order to reduce drying time.

The time needed for washing and drying pins is thereby reduced, increasing the throughput of the spotting instrument.

These and other features and advantages of the present invention will become readily apparent from the following detailed description wherein embodiments of the invention are shown and described by way of illustration of the best mode of the invention. As will be realized, the invention is capable of other and different embodiments and its several details may be capable of modifications in various respects, all without departing from the invention. Accordingly, the drawings and description are to be regarded as illustrative in nature and not in a restrictive or limiting sense with the scope of the application being indicated in the claims.

BRIEF DESCRIPTION OF THE DRAWINGS

For a fuller understanding of the nature, and objects of the present invention, reference should be made to the following detailed description taken in connection with the accompanying drawings wherein.

DETAILED DESCRIPTION OF PREFERRED EMBODIMENTS

The present invention is directed to a method and apparatus for quickly and efficiently washing and drying microarray spotting pins, particularly pins of the type having slot reservoirs. The invention, however, is not limited to such pins and can be used with a variety of pins including, e.g., solid pins, grooved pins, etc.

Briefly, the inventive apparatus comprises an integrated pin washer/vacuum dryer system that allows pins to be washed and dried while substantially in one position, i.e., without requiring significant movement of a printhead holding the pins between washing and drying cycles. Generally, in accordance with the invention, instead of dipping pins in a wash solution and diluting residual sample material in the slot reservoir of the pins as with the prior art, pins are washed by directing one or more streams of wash fluid at them with some velocity in a turbulent air environment. Actively flowing wash fluid on the pin circulates the fluid through the slot reservoir, causing rapid dilution of the residual sample, generally without need for intermediate drying. Streams directed horizontally at the side opening of the reservoir slot while air is flowing vertically at a similar velocity are particularly effective at removing residual sample. To dry the pins, a gas such as, air is flowed across pin surfaces.

Figure 7:
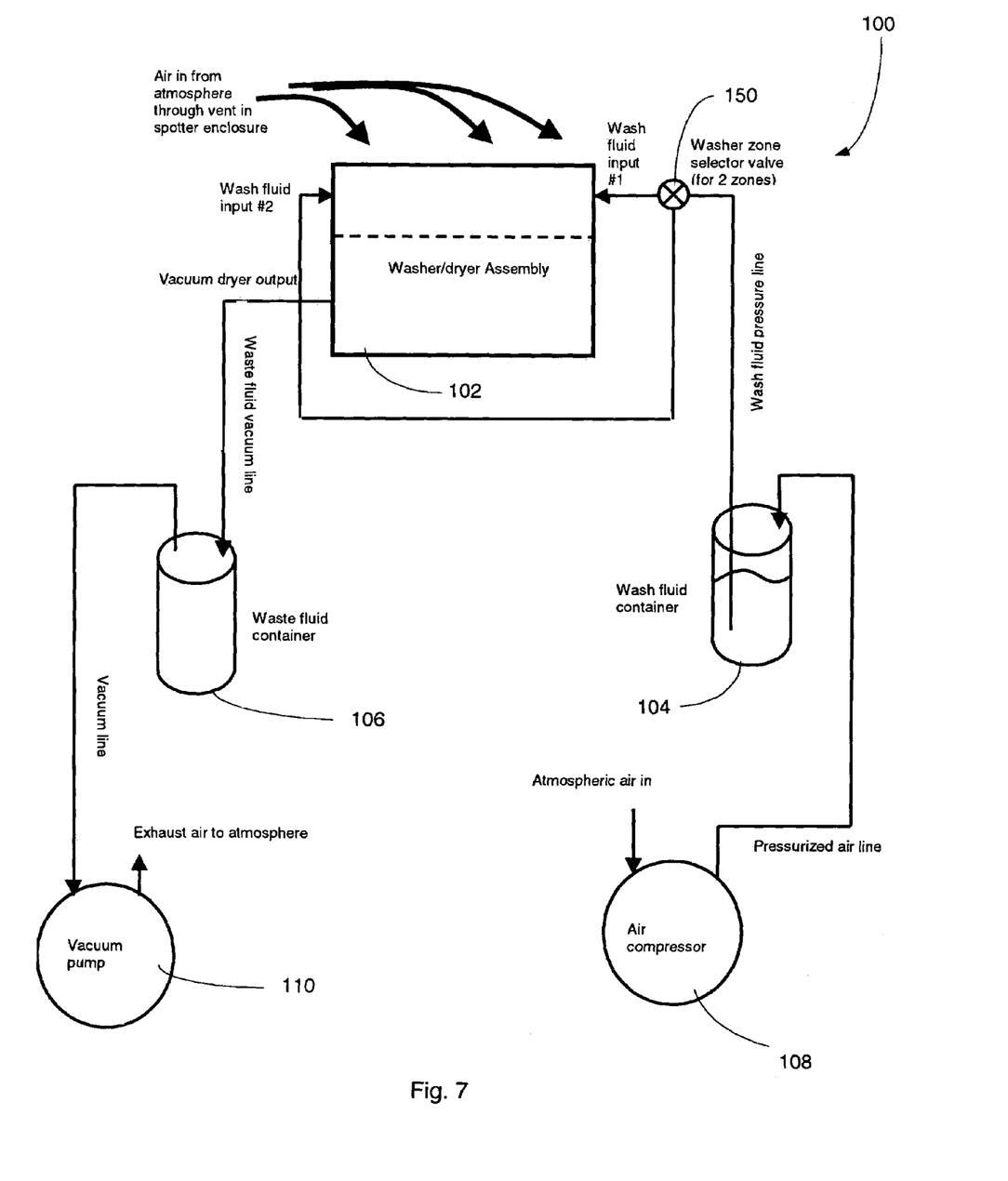
FIG. 7 is a simplified block diagram of a pin washer/dryer system in accordance with the present invention.

FIG. 7 is a block diagram of a pin washer/dryer apparatus 100 in accordance with the invention. The apparatus 100 includes a washer/dryer assembly 102, in which the pins are washed and dried as will be described below. Wash fluid from a wash fluid container 104 flows through the assembly 102 and is collected in a waste fluid container 106. Flow of wash fluid into the assembly 102 is pressurized by, e.g., an air compressor 108. A variety of other pressure applying devices can alternatively be used including, e.g., gear, peristaltic or other types of liquid pumps applied directly to the wash fluid. A vacuum is applied to draw wash fluid and air from the assembly 102 using, e.g., a vacuum pump 110.

Figure 8A:
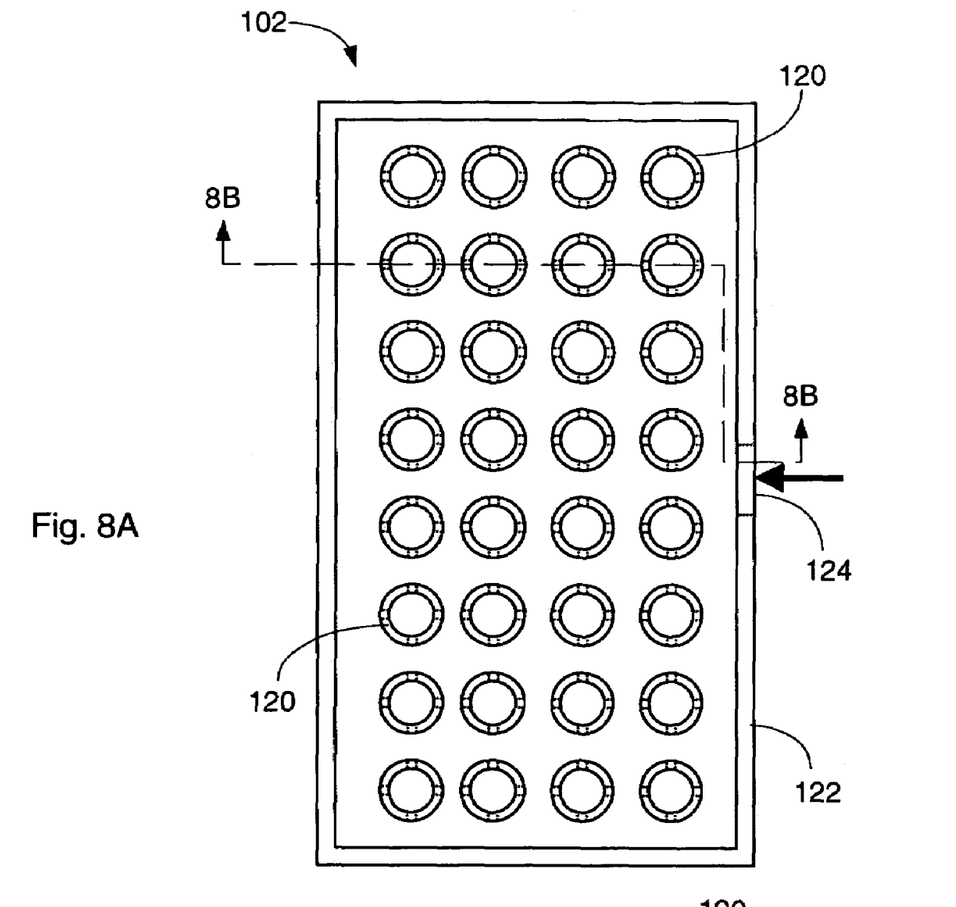
FIG. 8A is a top view of a washer/dryer assembly of the washer/dryer system in accordance with the present invention.
Figure 8B:
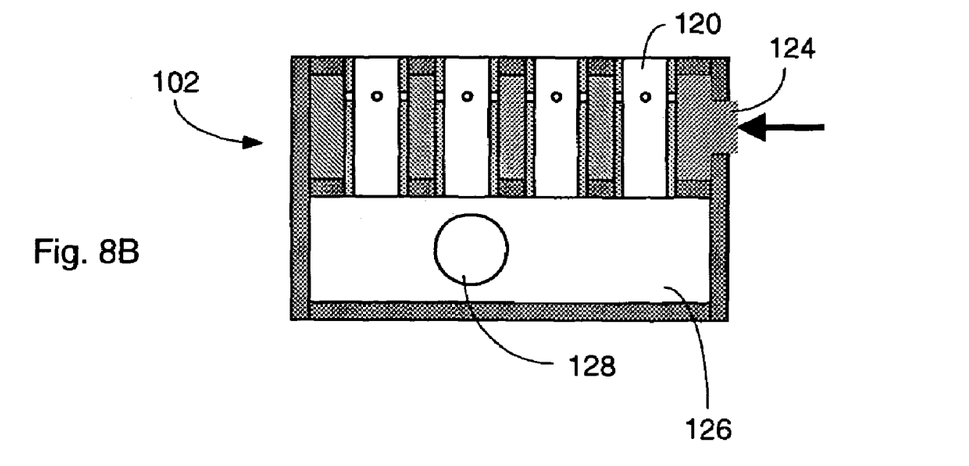
FIG. 8B is a cross-section view of the washer/dryer assembly taken generally along line 8B-8B of FIG. 8A.

FIGS. 8A and 8B show top and front cross-section views, respectively, of a representative washer/dryer assembly 102. The assembly 102 includes a structure comprising an array of upstanding tubes 120 arranged in a housing 122. As will be described below, each tube 120 defines a pin chamber configured to receive a pin tip. The assembly 102 shown in the drawings is designed for washing pins in a 32 pin printhead. This is exemplary only as a washer/dryer assembly in accordance with the invention can be made in a variety of sizes to accommodate different sized printheads. The assembly 102 includes one or more wash fluid input ports 124 for receiving wash fluid from the container 104. As shown in FIG. 8B, the assembly 102 also includes a receptacle, more particularly a vacuum plenum chamber, 126 from which waste wash fluid and air from the tubes are withdrawn through a vacuum port 128. A vacuum line from the waste fluid container 106 is connected to the port 128.

Figure 9A:
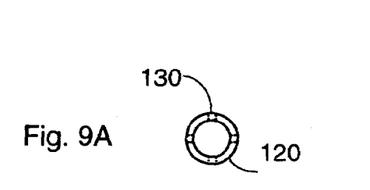
FIG. 9A is a top view of a tube of the washer/dryer assembly in accordance with the invention.
Figure 9B:
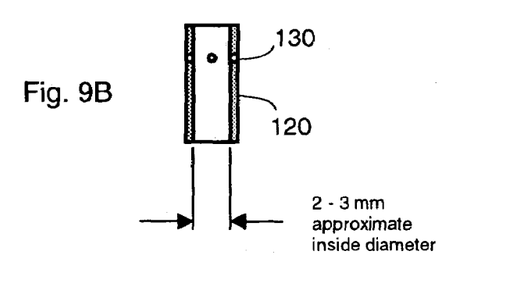
FIG. 9B is a cross-section view of the FIG. 9A tube.

FIGS. 9A and 9B are top and cross-section views, respectively, of a representative tube 120 in the washer/dryer assembly 102. As discussed below, each tube includes openings for flow of wash fluid and gas therethrough. The wall defining the tube 120 includes one or more wash fluid inlet ports 130. The preferred embodiment includes four inlet ports 130, and four streams of wash fluid enter the tube 120 through the ports 130. When wash fluid under positive pressure is applied to the outer wall of this tube 120, the fluid enters through the ports 130 in streams (indicated by arrows 132 in FIG. 10 impinging upon a pin tip inserted in the tube 120. The wash fluid ports 130 are preferably aligned so that two of the ports 130 produce streams that are parallel to the slot 30 in the pin. The wash fluid streams are directed to strike the pin tip at or near the root of the pin slot 130 when a pin is inserted in the tube.

The inner diameter of the tube 120 is in the range of about 1.5-2.5 times the diameter of the largest portion of the pin tip inserted in the tube. With a pin diameter of 1.5 mm, tubes with inner diameters of 2.2 to 3.0 mm have been found to be effective. Also wash fluid ports 130 having 250 micron and 350 micron diameters have been found to be effective, although larger and smaller ports can also be used. The wall thickness can have a fairly wide range, e.g., 250 microns to 500 microns. The tube 120 preferably comprises stainless steel hypodermic tubing material, e.g., of type 316W or type 304 stainless steel. Such tubing is available, from, e.g., Small Parts, Inc., Miami Lakes Fla. 33014 (sample part numbers O-HTXX-12 and Q-HTXX-9).

Figure 11:
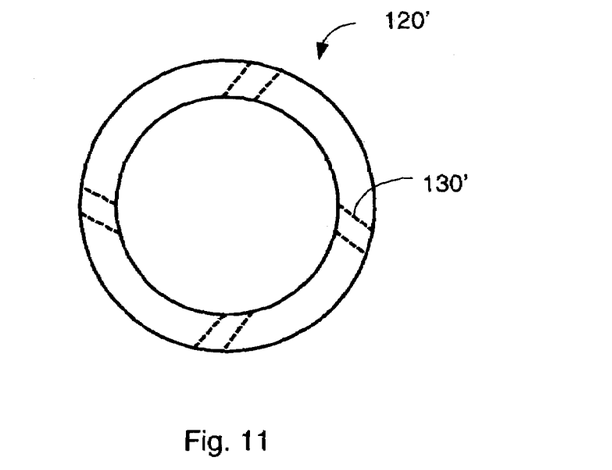
FIG. 11 is a top view of an alternative tube in accordance with the invention.
Figure 12:
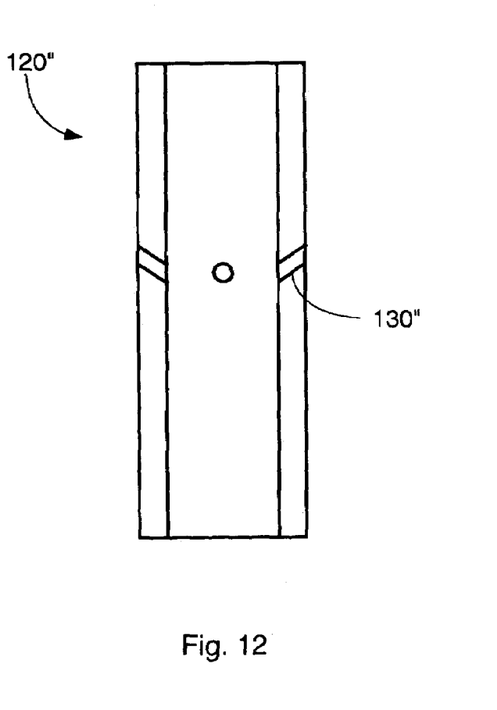
FIG. 12 is a cross-section view of another alternative tube in accordance with the invention.
Figure 13:
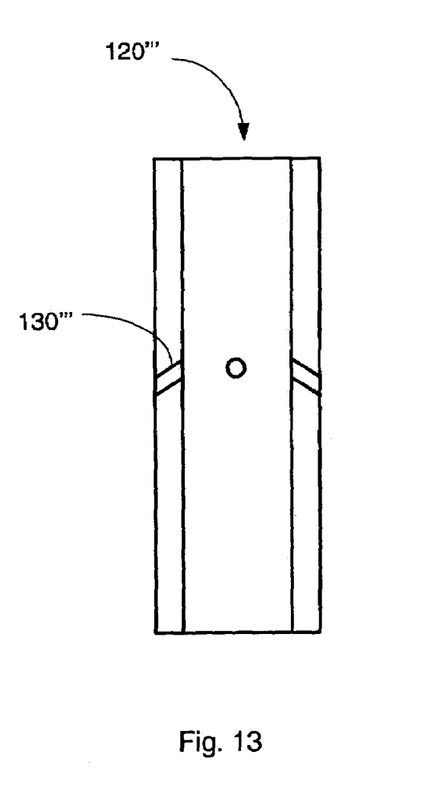
FIG. 13 is a cross-section view of yet another alternative tube in accordance with the invention.

In the tube 120, the inlet ports 130 are configured such that wash fluid is directed generally radially towards the center of the tube. Other inlet port configurations are also possible. For example, FIG. 11 is a top view of an alternative washer/dryer tube 120' in accordance with the invention. Unlike the tube 120 shown in FIGS. 9A, 9B, and 10, the tube 120' includes wash fluid ports 130' that are oriented in a slightly off-center direction, i.e., the wash fluid ports 130' are angled to direct wash fluid in a direction away from the tube center, creating a swirling wash pattern. The wash fluid ports can also be oriented in various other directions. For example, FIG. 12 shows a tube 120" having wash fluid ports 130" angled downwardly. FIG. 13 shows a tube 120'" having wash fluid ports 130'" angled upwardly. Although not shown, tubes could also be provided with wash fluid ports that are angled upwardly or downwardly in combination with an off-center orientation.

Different types of pins protrude from the bottoms of the printheads various distances, ranging from about 10 mm to about 20 mm. It is advantageous to retain a clearance between the bottom of the printhead and the top of the washer/dryer assembly of at least 3 mm, and preferably 6 or 7 mm. When the drying function (as described below) is activated, a large volume of air (indicated in FIG. 10 by arrows 134) flows into the space between the bottom of the printhead and the top of the washer/dryer assembly. A sufficient clearance allows air flow without a large pressure drop.

Washing times (the time during which fluid streams are expelled from the wash fluid ports 130) can vary, e.g., from 0.5 to about 3 seconds, depending on the type of wash fluid, the pressure of the wash fluid, and the diameter of the wash fluid ports. With the tube dimensions described above and using water as' the wash fluid, wash fluid pressure in the range of 5-10 psi, which induces wash fluid velocity of about 3-6 m/sec from each port at a flowrate of about 0.07-0.15 cc/sec from each port, has been found to be effective.

Figure 10:
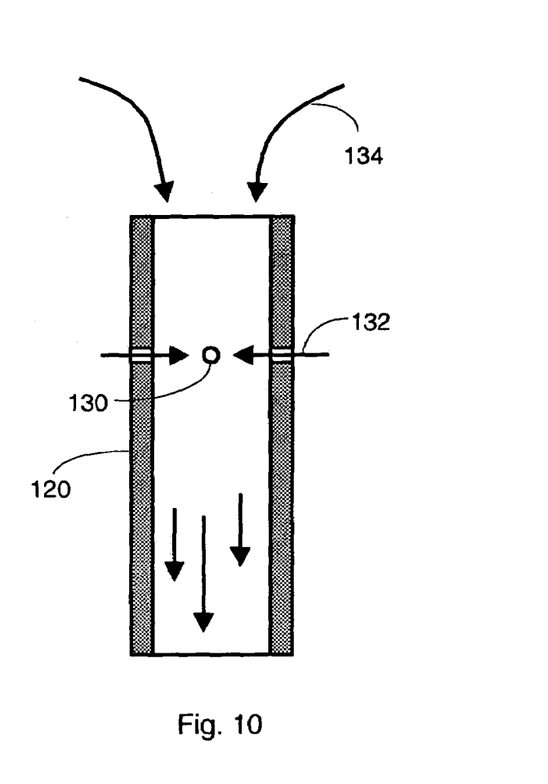
FIG. 10 is an enlarged cross-section view of the tube, illustrating fluid flow therethrough.

A moderate vacuum is preferably applied to the bottom of the tube during pin washing, producing air flow simultaneous with the wash fluid stream introduction as shown in FIG. 10. The vacuum directs the wash fluid down and out of the tube toward the vacuum plenum chamber 126 of the assembly 102 rather than up toward the printhead. Pins are typically slidably mounted in printheads. The mechanical tolerances of the pins sliding in the printhead are such that even a little wash fluid on the shaft of the pin where it slides in the printhead will cause the pin to stick. Therefore, sufficient vacuum to inhibit wash fluid from flowing or splashing out of the top of the tube toward the printhead is advantageous. Also, the airflow during washing imparts tangential velocity to the wash fluid on the pin surface increasing the effectiveness of washing. However, a limited vacuum is applied as high air velocity (over about 10 m/sec.) can cause the wash streams to deviate away from the pin and into the direction of air flow. If the air velocity is too high and wash fluid velocity too low, the wash fluid can flow down the inside of the tube without contacting the pin. During the washing step, vacuum sufficient to produce air velocity in the range of 0.1 to about 5 m/sec in the tubes is sufficient to entrain the wash fluid without excessively deviating the streams away from the pin.

If a user desires to apply a high vacuum (e.g., a full drying vacuum as used in the subsequent drying process) during pin washing to further increase washing turbulence, the wash fluid pressure is increased so that the wash fluid stream velocity is sufficient to allow the stream to traverse the cross-flowing air stream and strike the pin. Insufficient wash fluid pressure in this case can cause the wash fluid to stay in contact with the tube's inner wall, and simply run down the inside diameter of the tube without sufficiently contacting the pin. Wash fluid pressure above about 20 psi with the tube dimensions described above is sufficient to drive the wash streams against the pin even with a full drying vacuum activated.

In ordinary operation of the washer/dryer assembly 102, wash fluid is delivered to all washer-dryer tubes 120 in the assembly simultaneously, regardless, of whether or not a pin has been installed in the printhead position corresponding to each tube. Printheads are often not fully populated with pins for various reasons. (For instance, a user might not wish to create a microarray with a large footprint, thereby easing the control of hybridization downstream.) In order to avoid wastage of wash fluid, the system is optionally configured to supply wash fluid to only select tubes or groups of tubes in the assembly. For this purpose, the assembly housing is optionally equipped with internal barriers to separate tubes or group of tubes into zones such that fluid is supplied only to particular zones in the assembly as desired. As illustrated in FIG. 7, the assembly is optionally provided with multiple wash fluid input ports, each leading to a respective zone. One or more washer zone select valves 150 are provided to control wash fluid flow to each zone.

After the washing process, the pressure on the wash fluid is removed, causing the flow of the streams through the wash fluid ports in the tubes to stop. The vacuum for drying the pins is then applied by the vacuum pump 110, causing air to flow through the annular gap between the pins and the tube walls. Vacuum sufficient to produce air velocities of about 50 m/sec or more effectively dries pins in a few seconds. The following table shows examples of two apparatus designs that dry water from "Telechem Chipmaker 2" pins in two seconds or less, with ambient humidity about 40% RH:

|  | Washer Tube I.D. 2.3 mm | Washer Tube I.D. 3.0 mm |
|---|---|---|
| Number of washer tubes in wash/dry assembly | 48 | 48 |
| Area of each tube I.D. | 4.2 mm$^2$ (0.006 in$^2$) | 7.1 mm$^2$ (0.011 in$^2$) |
| Total area of all tubes | 202 mm$^2$ (0.31 in$^2$) | 340 mm$^2$ (0.53 in$^2$) |
| Pump Model | Gast Regenair R1102 | Gast Regenair R4110-2 |
| Volume flow rate of air | 46 m$^3$/hr (27 cfm) | 156 m$^3$/hr (92 cfm) |
| Average velocity of air in tubes | 64 m/sec | 128 m/sec |

Many types of vacuum pumps are available including, e.g., rotary vane, linear piston, diaphragm, and other types. Regenerative blower type pumps are particularly suitable for generating the flow rates and velocities above. The vacuum pumps used in the above tests were the Gast Regenair Models R1102 (27 cfm) and R4110-2 (92 cfm), from both the Gast Manufacturing Corporation, Benton Harbor Mich. 49023.

To move air at these flow rates, the valves, fittings, tubes, etc. that are between the vacuum pump 110 and the washer/dryer assembly 102 are configured not to excessively restrict the air flow. One guideline to avoid excessive air flow restriction is to design the cross-sectional area of the tubes, fittings, etc. to be at least as large as the total area of all of the tubes 120 in the washer/dryer. In the case of the 2.3 mm tubes and a 48-pin assembly used in the table above, that total area is about 202 mm$^2$ (0.31 in$^2$). (A single circular cross section with that area is about 16 mm or 0.63 inches in diameter.) The configuration with the 3 mm diameter tubes and 92 cfm vacuum pump in the table above operates with only 1.5" mercury air pressure drop across the washer/dryer assembly using these guidelines.

The wash fluid with the residue washed from the pins is removed from the washer/dryer assembly 102 by the vacuum system. This liquid is separated from the air before it reaches the vacuum pump 110. This is accomplished by directing the mixed air/wash fluid stream to the container 106 where the air velocity slows sufficiently to allow the liquid to settle to the bottom. A 5.25-gallon polymer lab carboy (available from Cole Parmer P-06063-22, Cole Parmer Instrument Co., Vernon Hills Ill. 60061) with fill-vent caps is an example of a suitable container 106. The incoming mixed air/wash fluid stream is directed through a cap of the container 106 downward towards the bottom. An air outlet to the vacuum pump is at the top of the container (also in the capy and draws in air with very little wash fluid mixed in.

Various modifications to the wash-dry cycle described above are possible. For example, instead of applying the multiple-jet wash once followed by a thorough drying, a plurality of quick pulse-type wash actions can be applied to the pin with some drying between wash pulses. For pins that can only take wash fluid into the slot via capillary action, this multi-pulse wash cycle could be advantageous in serially diluting the residue in the slot.

It also may be advantageous to utilize the printhead's motion control system to impart small motions to the pins during the wash/dry process. Moving the pins vertically (along the pin axes) a few millimeters or transversely a fraction of a millimeter or so can further increase the turbulence of the wash fluid flow on the pin surface. A small vertical move between the wash and dry operations may also enhance pin drying by placing the pin tip in a location in the tube that has higher air turbulence. Small motions such as these take only a fraction of a second and do not significantly add to the wash/dry cycle time.

The inventive washer/dryer system can be used with multiple types of wash fluids as desired. For example, pins could be washed with a detergent solution followed by a water rinse. Also, instead of a steady stream of wash fluid directed to pins, wash fluid can be delivered in pulses by rapidly opening and closing a valve at the wash fluid input to the washer/dryer assembly 102. Alternatively, an aerosol of wash fluid could be used by injecting pressurized air or other gas into the wash fluid.

Figure 14:
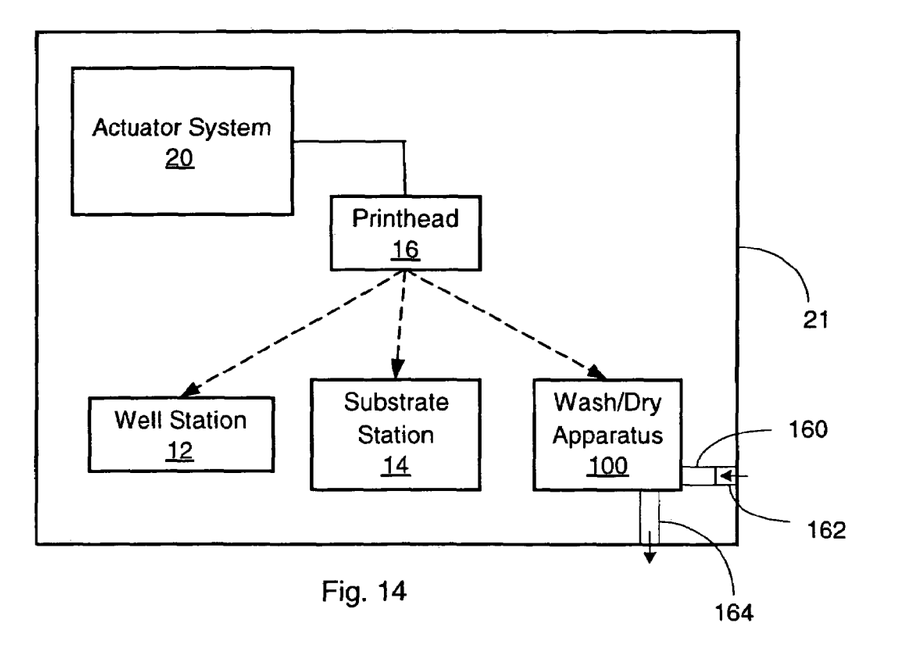
FIG. 14 is a simplified block diagram of a microarray spotting instrument in accordance with the invention illustrating dryer air venting.

As previously mentioned, the environment inside the microarray spotter enclosure generally has controlled humidity in the 55%-65% range. The vacuum drying process in accordance with the invention is preferably made quicker and more effective by allowing the pin washer-dryer 100 to be primarily supplied with lower-humidity air from outside the enclosure as illustrated in the block diagram of FIG. 14. As previously mentioned, air in typical office and laboratory environments is in the 30%-45% range. By placing the washer-dryer apparatus 100 near an outside wall of the enclosure 21, it is relatively easy to configure a vent and ducting 160 in the enclosure 21 that allows outside air to be drawn in by the dryer of the apparatus 100. It is advantageous to place a filter 162 in this venting arrangement to reduce the entry of dust into the drying air stream. Air from the dryer is exhausted outside the enclosure through a ducting 164.

While air is described as the gas used for drying pins, it should be noted that use of other sourced gases is also possible. Such drying gases can include, e.g., dry nitrogen, heated air, or otherwise dried air.

Since certain changes may be made in the above apparatus without departing from the scope of the invention herein involved, it is intended that all matter contained in the above description or shown in the accompanying drawing shall be interpreted in an illustrative and not a limiting sense.

The invention claimed is:

1. A method of washing and drying a pin of a microarray spotting instrument, comprising:

moving said pin to a given position;

washing said pin while in said given position with a wash fluid while applying a vacuum to remove wash fluid previously applied to said pin; and drying said pin without substantially moving said pin from said given position, said pin being dried by applying a vacuum to draw air past said pin.

2. The method of claim 1 wherein moving the pin comprises positioning said pin in a given location in a pin washer/dryer apparatus.

3. The method of claim 2 wherein said given location comprises a chamber for receiving the pin.

4. The method of claim 3 wherein said chamber is defined by a tube.

5. The method of claim 1 wherein washing the pin comprises directing at least one stream of wash fluid at the pin.

6. The method of claim 5 wherein said stream velocity is approximately 3 m/sec.

7. The method of claim 5 wherein multiple streams of wash fluid are directed at a tip of said pin.

8. The method of claim 7 wherein the streams are directed in a swirling pattern.

9. The method of claim 1 wherein said position comprises a tube interior, and wherein washing the pin comprises directing a stream of wash fluid at the pin through an aperture in the tube.

10. The method of claim 1 wherein the air is flowed at a speed greater than 20 m/sec.

11. The method of claim 1 wherein said position comprises a tube interior, and wherein the vacuum to draw air is applied to the tube to draw air through the tube.

12. The method of claim 1 wherein said pin includes a pin tip having a slot reservoir for holding sample material to be deposited on a microarray substrate, and wherein washing the pin comprises directing a stream of wash fluid at the slot reservoir.

13. The method of claim 1 wherein washing the pin comprises impacting said pin with pulsed streams of wash fluid.

14. The method of claim 13 wherein washing further comprises at least partially drying said pin between applications of said pulsed streams of wash fluid.

15. The method of claim 1 wherein the air drawn past said pin is of lower humidity than air in an enclosure containing the spotting instrument.

16. The method of claim 1 wherein the vacuum applied to draw air past said pin is greater than the vacuum applied to remove wash fluid.

* * * * *